(12) United States Patent
Garamszegi et al.

(10) Patent No.: US 8,657,858 B2
(45) Date of Patent: Feb. 25, 2014

(54) BOTTOM-LOADING PEDICLE SCREW ASSEMBLY

(75) Inventors: Laszlo Garamszegi, Mission Viejo, CA (US); Kelvin Nguyen, Garden Grove, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 918 days.

(21) Appl. No.: 12/077,940

(22) Filed: Mar. 21, 2008

(65) Prior Publication Data

US 2008/0269809 A1    Oct. 30, 2008

Related U.S. Application Data

(60) Provisional application No. 60/920,211, filed on Mar. 26, 2007.

(51) Int. Cl.
*A61B 17/32* (2006.01)

(52) U.S. Cl.
USPC .......................................................... 606/278

(58) Field of Classification Search
USPC .................. 606/246–279, 300–308
See application file for complete search history.

(56) References Cited

U.S. PATENT DOCUMENTS

| | | |
|---|---|---|
| 5,534,027 A | 7/1996 | Hodorek |
| 5,578,034 A * | 11/1996 | Estes ............................. 606/281 |
| 5,876,402 A | 3/1999 | Errico et al. |
| 5,891,145 A | 4/1999 | Morrison et al. |
| 5,931,838 A | 8/1999 | Vito |
| 6,059,785 A | 5/2000 | Schavan et al. |
| 6,063,090 A | 5/2000 | Schlapfer |
| 6,113,601 A | 9/2000 | Tatar |
| 6,241,731 B1 | 6/2001 | Fiz |
| 6,261,291 B1 | 7/2001 | Talaber et al. |
| 6,280,442 B1 | 8/2001 | Barker et al. |
| 6,331,179 B1 | 12/2001 | Fried et al. |
| 6,485,491 B1 | 11/2002 | Farris et al. |
| 6,602,255 B1 | 8/2003 | Campbell et al. |
| 6,613,053 B1 | 9/2003 | Collins et al. |
| 6,663,635 B2 | 12/2003 | Frigg et al. |
| 6,716,214 B1 | 4/2004 | Jackson |
| 7,001,389 B1 | 2/2006 | Navarro et al. |
| 7,048,739 B2 | 5/2006 | Konieczynski et al. |
| 7,087,057 B2 | 8/2006 | Konieczynski et al. |
| 8,257,396 B2 * | 9/2012 | Jackson ........................ 606/246 |
| 2002/0026193 A1 | 2/2002 | Barker et al. |
| 2004/0097933 A1 | 5/2004 | Lourdel et al. |
| 2004/0116929 A1 | 6/2004 | Barker et al. |
| 2005/0049593 A1 * | 3/2005 | Duong et al. .................... 606/69 |
| 2005/0261687 A1 | 11/2005 | Garamszegi et al. |
| 2006/0142761 A1 * | 6/2006 | Landry et al. ................... 606/61 |
| 2007/0270813 A1 | 11/2007 | Garamszegi |
| 2008/0045953 A1 | 2/2008 | Garamszegi |

* cited by examiner

*Primary Examiner* — David Isabella
*Assistant Examiner* — Marcia Hoffman
(74) *Attorney, Agent, or Firm* — Michael J. Loi

(57) ABSTRACT

A spine screw assembly is adapted to be loaded from a bottom of a receiver member. The spine screw assembly includes a bone fastener with a head having a groove that removably accepts a clip. The clip acts to retain the head of the bone fastener in the receiver member.

5 Claims, 9 Drawing Sheets

BOTTOM-LOADING PEDICLE SCREW ASSEMBLY

REFERENCE TO PRIORITY DOCUMENT

This application claims priority of U.S. Provisional Patent Application Ser. No. 60/920,211 filed Mar. 26, 2007. Priority of the aforementioned filing date is hereby claimed and the disclosures of the Provisional Patent Application is hereby incorporated by reference in its entirety.

BACKGROUND

This disclosure is directed to skeletal bone fixation systems, and more particularly to a fixation assembly for vertebrae of a spinal column.

Spinal fixation systems are used to secure sections of the spinal column, such as vertebral bodies, into a fixed position to correct spinal injuries and defects. Internal fixation is used most frequently in the spine in conjunction with vertebral fusion, and also for the manipulation of the spine to correct spinal deformities. A typical spinal fixation assembly includes a fixation device, such as a screw or hook, that can be attached to a portion of a first vertebral body. The screw can be coupled to a stabilization member, such as an elongate rod, that can be linked to one or more additional vertebral bodies using additional screws.

Pursuant to a general process, two or more bone screws and/or hooks are secured to a vertebral body that is to be stabilized. After the screws are secured to the vertebral bodies, the screws are coupled to a spinal stabilization rod that restricts movement of the stabilized vertebra. It is important that the screws have a secure coupling with the spinal stabilization rod in order to prevent movement of the rod relative to the screw after placement.

In several available pedicle screw systems, a tulip-like coupling element with opposing upright arms or walls is used to secure the pedicle screw to the rod. The coupling element and pedicle screw are configured to be coupled to an elongate stabilizer, such as a rod, that is positioned above the head of the pedicle screw. A compression member, such as a compression nut, is configured to mate with the coupling element and provides a compressive force to the rod. The rod is then forced against the head of the pedicle screw, and that force is translated to the coupling element. Accordingly, the forces generated by the compression nut clamp the rod and pedicle screw head together within the coupling element.

One type of pedicle screw system is a bottom-loaded system wherein the screw is loaded into the coupling element through the bottom of the coupling element. Bottom loading can allow for greater flexibility and adjustment of the coupling element relative to the screw. There is a need for improved bottom-loaded pedicle screw systems.

SUMMARY

Disclosed is a spine screw assembly such as a pedicle screw system. In an embodiment, the spine screw assembly comprises: a fastener having an upper end and a lower end, a head at the upper end, and an anchoring element extending between the upper and lower ends, wherein a groove is positioned in the head of the fastener; a clip sized to be positioned in the groove, wherein the annular clip transitions between a first state of increased size and a second state of decreased size, and wherein the annular clip can be locked within the groove when in the second state of decreased size and can be removed from the groove by transitioning the first state of increased size; a coupling element having an upper opening at an upper end and a lower opening at a lower end, the coupling element including a rod receiving channel adapted to receive a stabilizing rod, a bore extending through the lower end of said coupling element for receiving said fastener, and a seat adapted to engage the head when the fastener is positioned in the bore; and a compression nut engageable with the coupling element, the compression nut adapted to rotatingly move distally into the coupling element to translate a force to the head of the fastener such that the head is forced against the seat of the coupling element to prevent relative movement between the fixation element and the coupling element.

Other features and advantages will be apparent from the following description of various embodiments, which illustrate, by way of example, the principles of the disclosed devices and methods.

DETAILED DESCRIPTION

Figure 1A:
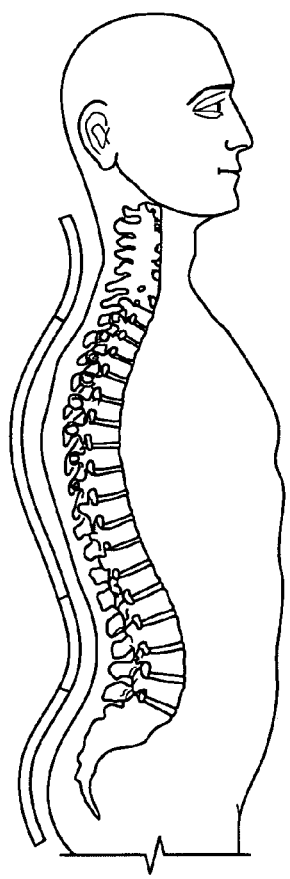
FIG. 1a is an illustration of a human vertebral column.

Before discussing the embodiments in detail, it may be helpful to first briefly review the basic devices and concepts used in orthopedic surgery, and particularly spine surgery. Bone stabilization assemblies are commonly used throughout the skeletal system to stabilize broken, fractured, diseased or deformed bones. In particular, pedicle screw systems are particularly well adapted for the fixation and manipulation of the bones of the vertebral column (FIG. 1a).

Figure 1B:
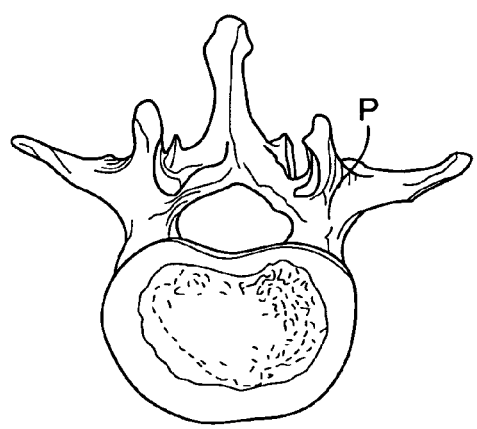
FIG. 1b is a superior view of a typical human vertebra.
Figure 1C:
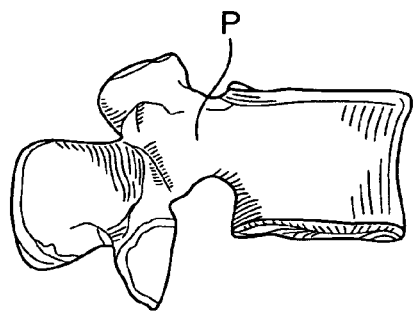
FIG. 1c is a lateral view of the vertebra depicted in FIG. 1b.

A vertebral pedicle is a dense stem-like structure that projects from the posterior of a vertebra. There are two pedicles per vertebra that connect to other structures (e.g. lamina, vertebral arch). The location of a pedicle P is illustrated in FIGS. 1b and 1c, which illustrate a typical vertebral column, a superior view of a typical vertebra, and a lateral view of a typical vertebra, respectively.

Bone screws have been used in spinal instrumentation since the 1960s. A pedicle screw is a particular type of bone screw designed for implantation into a vertebral pedicle. Monoaxial pedicle screws are still used quite often, but the current standard for implantation is a polyaxial pedicle screw made of titanium or titanium alloy. Titanium alloy is useful because it is highly resistant to corrosion and fatigue, and is MRI compatible. The screw is threaded and the head is moveable, allowing it to swivel so as to defray vertebral stress. Polyaxial pedicle screw lengths range from about 30 mm to about 60 mm with diameters ranging from about 5.0 mm to about 8.5 mm.

Figure 2:
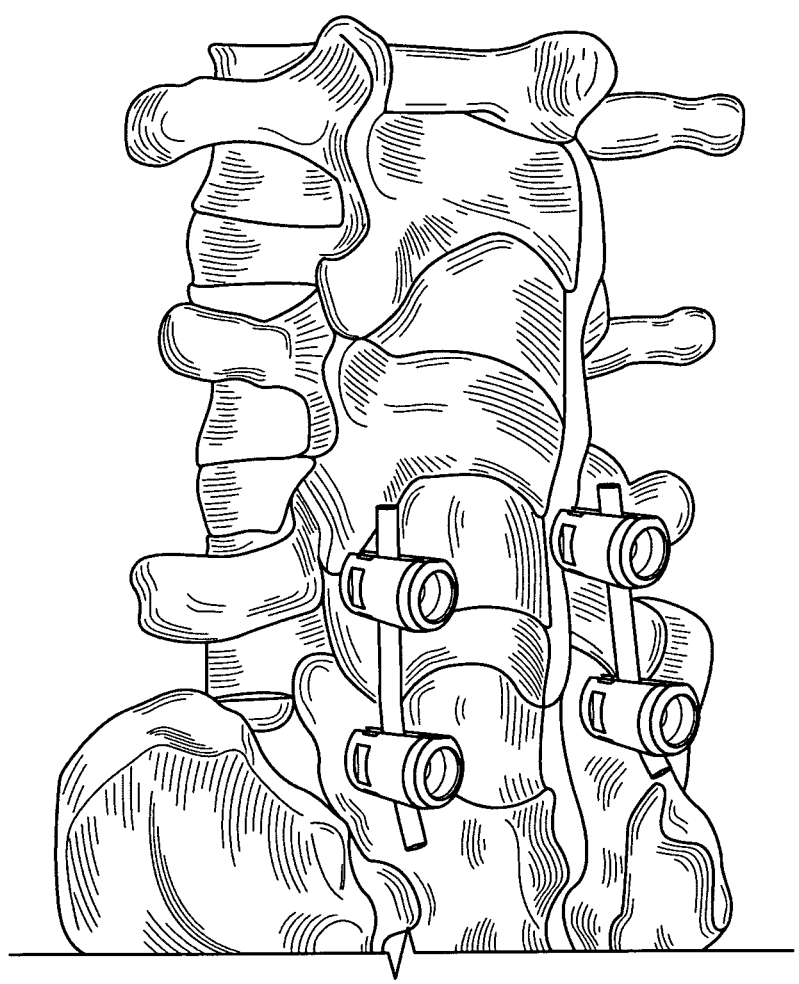
FIG. 2 is an illustration of a set of pedicle screws implanted into a human vertebral column.

Pedicle screws are used to correct deformity, and or to treat trauma. They can be used in instrumentation procedures to affix rods and plates to the spine. They can also be used to immobilize part of the spine to assist fusion by holding bony structures together. Although pedicle screws are most often used in the lumbar (lumbosacral) spine, they can be implanted in the thoracic and sacral vertebra. The surgeon uses fluoroscopy, conventional x-ray, and sometimes computer-assisted visualization to determine the depth and angle for screw placement. A receiving channel is drilled and the screw is inserted. The screws themselves do not fixate the spinal segment, but act as firm anchor points that can then be connected with a rod. As shown in FIG. 2, the screws are placed down the small bony tube created by the pedicle on each side of the vertebra, between the nerve roots. This allows the screws to grab into the bone of the vertebral body, giving them a solid hold on the vertebra. Once the screws are placed, one in each of the two pedicles of each vertebra, they are attached to metal rods that connect the screws together. The screws are placed at two or more consecutive spine segments (e.g., lumbar segment 5 and 6) and connected by the rods.

Generally, a poly-axial pedicle screw assembly includes a tulip-like coupling element that can be coupled to a fixation element, such as, for example, a pedicle screw, with a shaft and a head. Poly-axial pedicle screw assemblies can be top-loading and/or bottom-loading assemblies. In a top-loading assembly, the shaft of the fixation element is fed through the top of the coupling element. In bottom-loading assemblies, the head of the fixation element is inserted through the bottom of the coupling element.

Figure 3:
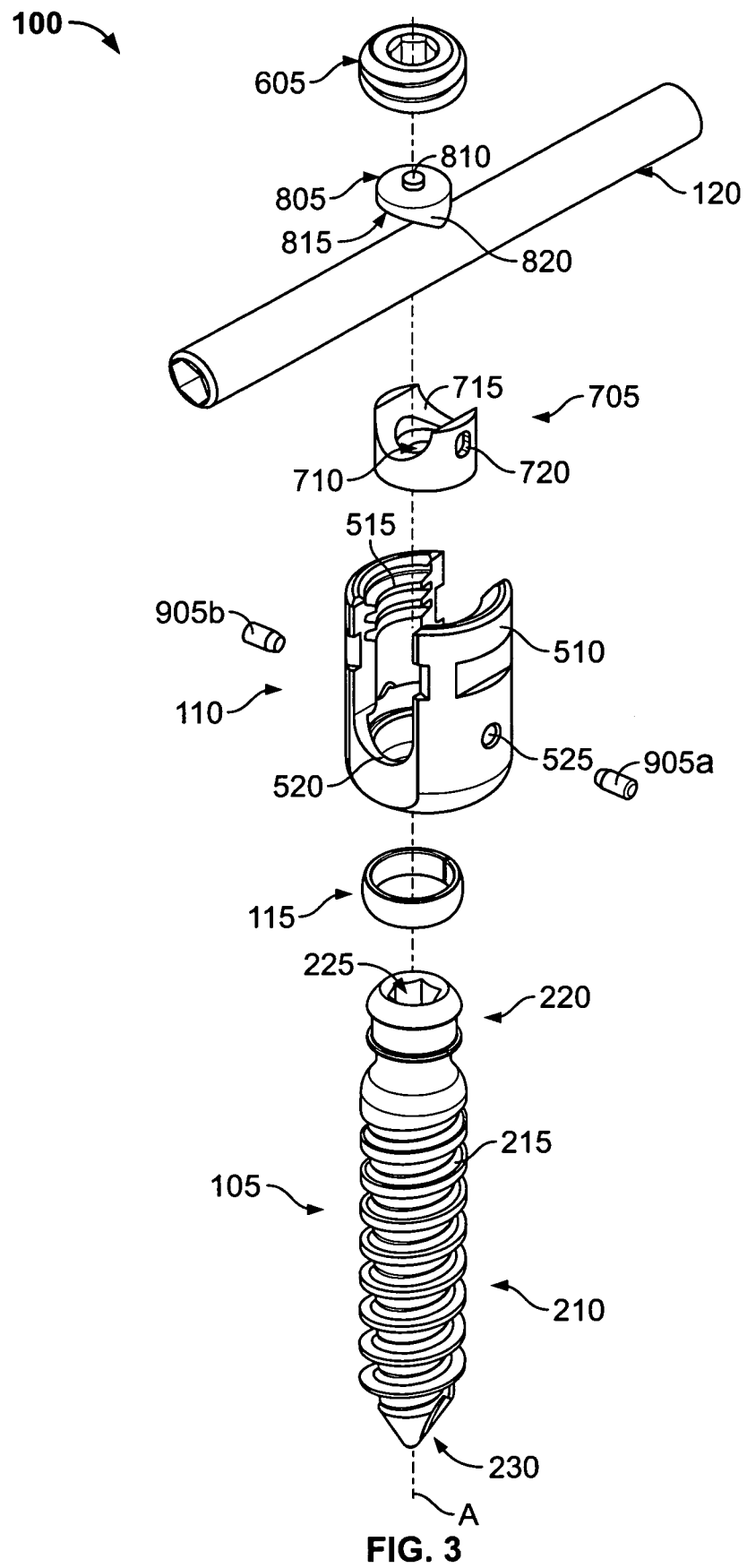
FIG. 3 shows an exploded view of a bone fixation assembly according to one embodiment.

FIG. 3 shows an exploded view of one embodiment of a bottom-loading polyaxial pedicle screw assembly. The assembly 100 generally includes a fixation element 105 that is removably coupled to a coupling element 110 and a clip 115 that is removably coupled to the fixation element 105. As described in detail below, the fixation element 105 can be coupled to a skeletal structure, such as a spinal vertebra. The coupling element 110 is used to couple the fixation element 105 to a stabilizer, such as an elongate rod 120, which can be coupled to multiple fixation elements using additional couplers.

The Fixation Element

Figure 4A:
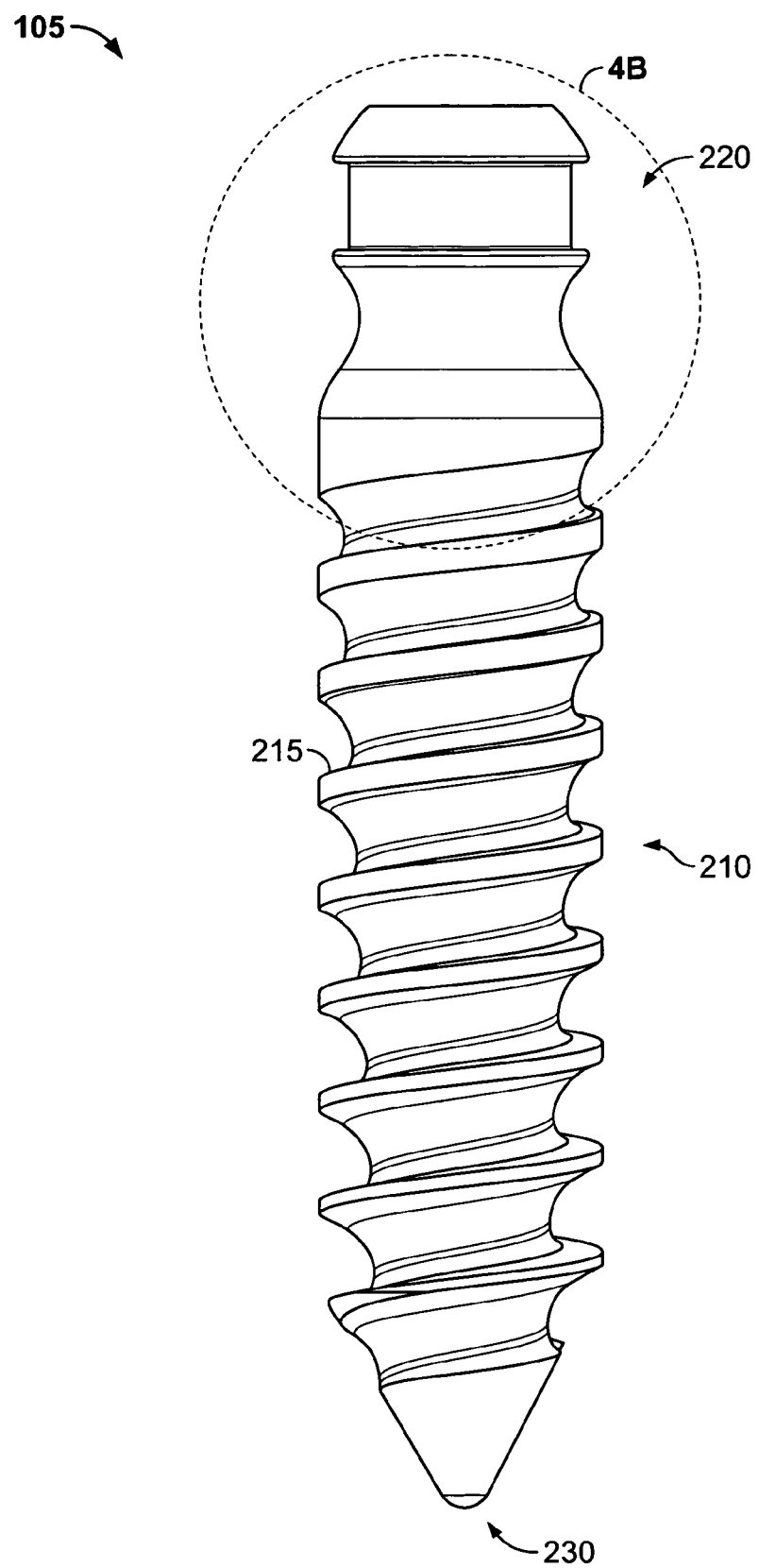
FIG. 4A is a lateral view of a bone fixation element according to one embodiment.

FIG. 4A shows a detailed view of a fixation element. The fixation element 105 can comprise, for example, an elongate screw having a threaded shank 210 with external threads 215 that can be screwed into a bone structure, e.g., pedicle of a vertebra. A head 220 is positioned at the proximal end of the shank 210.

Figure 4B:
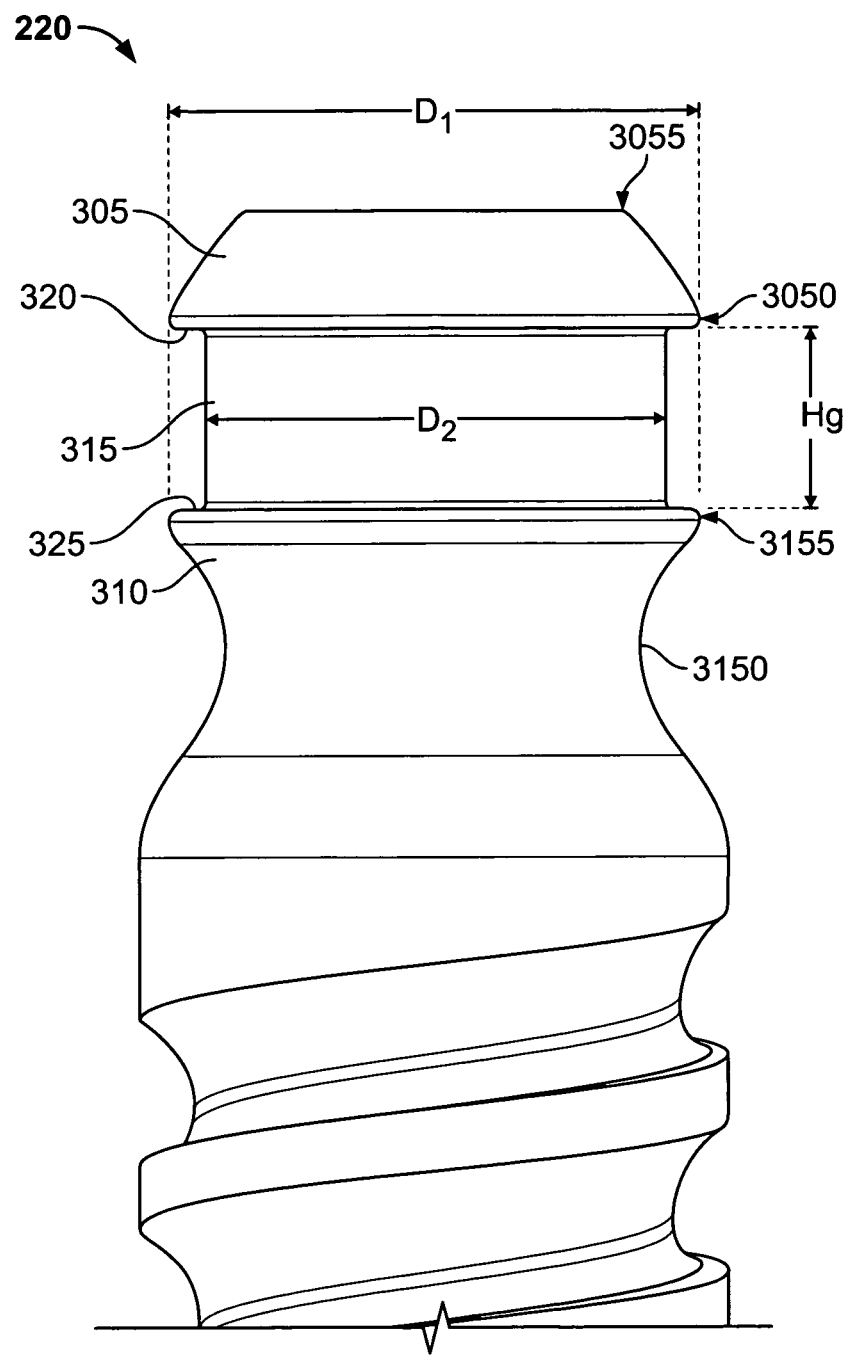
FIG. 4B is a lateral close-up view of a bone fixation element taken at circle 4B of FIG. 4A.

FIG. 4B shows a close-up view of the head 220 taken along circle 4B of FIG. 4A. The head 220 has an upper region 305 and a lower region 310 with a groove 315 therebetween. The upper region 305 and lower region 310 each has a distal end 3050, 3150 and a proximal end 3055, 3155. The distal end 3050 of the upper region 305 has a diameter D1 (which can essentially be equal to the diameter of the proximal end 3155 of the lower region 310). The groove 315 has a diameter D2, which is less than D1. Thus, a lip 320 overhangs the groove 315 at its proximal end and lip 325 juts out from underneath the groove 315 at its distal end.

In an embodiment, the upper region 305 and the lower region 310 are generally curved or spherical in shape, whereas the groove 315 is generally cylindrical in shape. It should be appreciated that other shapes of the upper and lower regions can be used. Similarly, other shapes of the groove can be used. The groove 315 has a shape that is configured to mate with and receive a correspondingly-shaped clip 115 therein, to be discussed in more detail below.

A drive coupler, such as a drive cavity 225 (best shown in FIG. 3) is located within or on the head 220 of the fixation element 105. The drive cavity 225 has a shape that is configured to receive a device that can impart rotational movement to the fixation element 105 in order to screw the fixation element into a bone structure. For example, the drive cavity 225 can have a hexagonal shape that is configured to receive therein an Allen-style wrench.

It should be appreciated that the drive coupler need not be a cavity that mates with an Allen-style wrench and that other types of drive couplers can be used. Moreover, the fixation element 105 can be in forms other than a shank 210, including, for example, a hook or clamp. Indeed, it should be appreciated that any structure or component configured for attachment to a bone structure can be used in place of the shank 210 of the fixation element 105.

The fixation element 105 can be made of various materials, including metallic and non-metallic material, depending on the application involved and the stresses expected in vivo. In one embodiment, the fixation element 105 is made of implant grade titanium (Ti-6A1-4V) per ASTM F-136.

The Clip

Figure 5A:
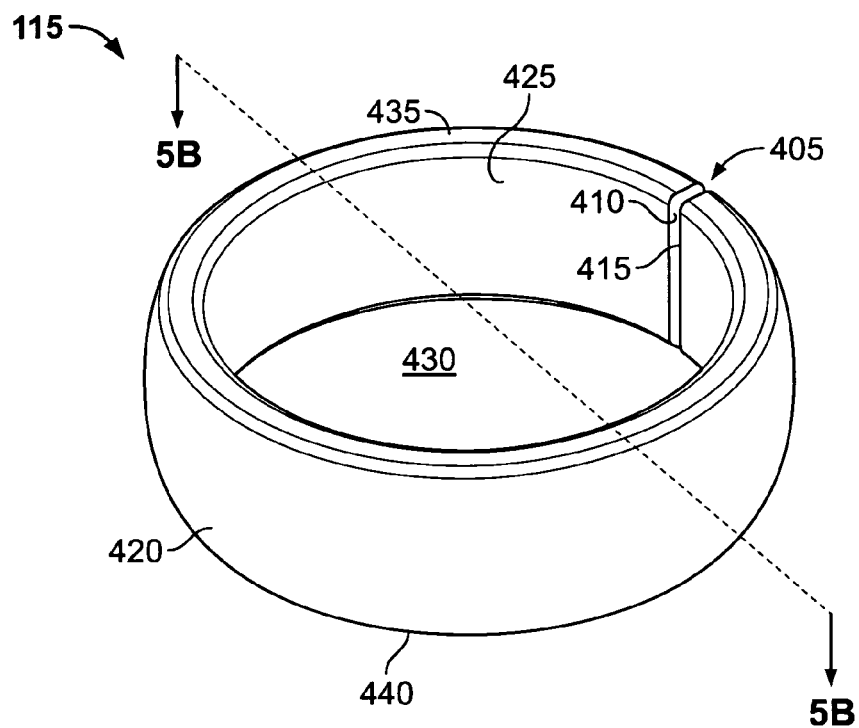
FIG. 5A is a perspective view of a clip according to one embodiment.
Figure 5B:
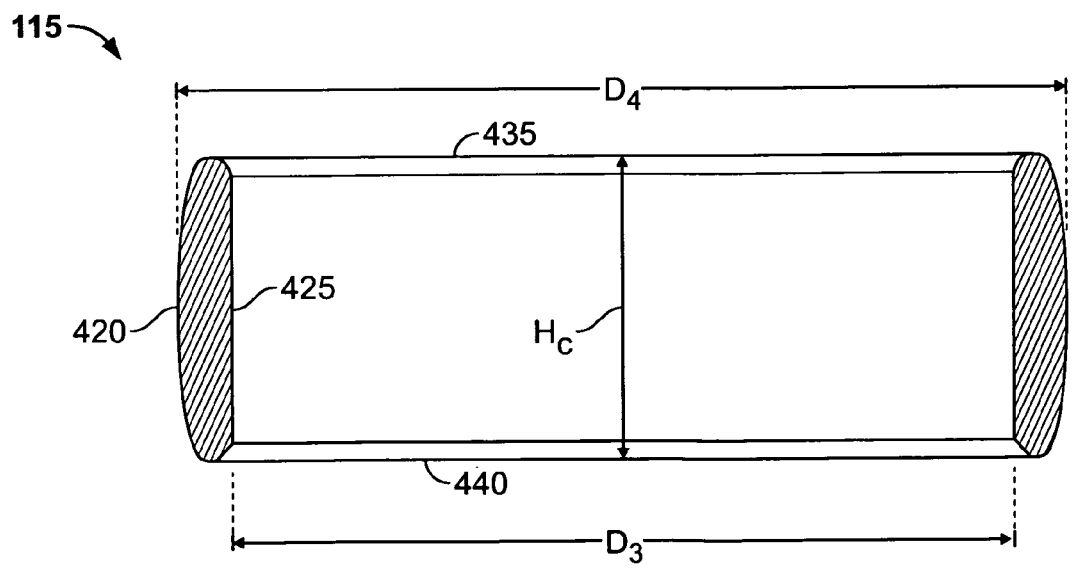
FIG. 5B is a cross-sectional view of the clip taken along lines B-B of FIG. 5A.
Figure 6:
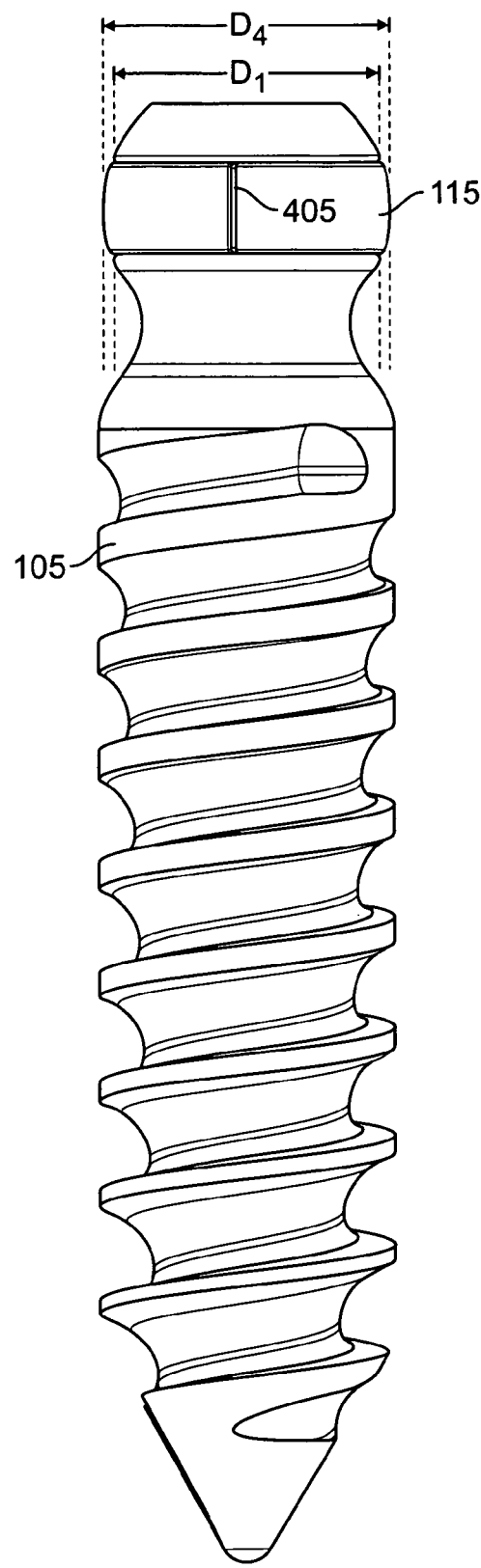
FIG. 6 is a lateral view of the clip of FIG. 5A installed in the bone fixation element of FIG. 4A.

As mentioned above, the groove 315 in the head 220 of the fixation element 105 has a shape that is configured to mate with and receive the correspondingly-shaped clip 115 therein. As shown in FIGS. 5A and 5B, the clip 115 is a generally annular ring having a break 405 in its circumference, wherein the break 405 defines two opposing ring surfaces 410, 415. The clip 115 can also take shapes that are not generally circular. The clip 115 has an outer diameter D4 and an inner diameter D3. Inner diameter D3 defines an opening 430 through which a fixation element 105 can be inserted.

The clip 115 has an outer surface 420 and an inner surface 425. As best shown in FIG. 5B, the outer surface 420 is generally curved or spherical in cross-section, whereas the inner surface 425 is generally flat in cross-section. This cross-section allows the clip 115 to mate with the generally cylindrical shape of the groove 315 at its inner surface 425 and complete the generally rounded shape of the head 220 at its outer surface 420.

The clip 115 is designed to be at least partially inserted into the groove 315 of the head 220. The height of the groove (Hg) is sufficient to receive the height of the clip (Hc), such that there is little play along axis A or in the up and down direction. Although there is little up and down play between the clip 115 and the groove 315, the clip 115 can be rotated around axis A inside the groove 315. Further, the width of the clip 115 is such that at least a portion of the clip 115 resides inside the groove 315 between upper lip 320 and lower lip 325 and a portion sits outside the groove 315. A portion of the proximal edge 435 of the clip 115 abuts the upper lip 320 of the head 220. Similarly, a portion of the distal edge 440 of the clip 115 abuts the lower lip 325 of the head 220.

The head 220 with the clip 115 residing in the groove 315 is configured to be inserted in the coupling element 110 from the bottom, as described in more detail below. While installed in the groove 315, the clip 115 can be radially compressed. The generally c-shape of the clip 115 and the slightly larger inner diameter D3 of the clip 115 compared to the groove 315 render the clip 115 flexible in the radial direction, also to be discussed in more detail below.

The clip 115 can be compressed until the opposing ring surfaces 410, 415 meet and the inner surface 425 of the clip 115 approaches the surface of the groove 315. During compression, the inner diameter D3 of the clip 115 decreases until it approaches the diameter D2 of the groove 315. Similarly, the outer diameter D4 of the clip 115 decreases until it approaches D1. This compression of the clip 115 allows the head to be inserted through the entry port near the bottom of the coupling element 110 into internal bore 505. Assembly of the device according to a bottom-loading configuration that involves compression of the clip 115 is to be discussed in more detail below.

Following compression, the clip 115 can resume its original shape such that the ring surfaces 410, 415 separate and the inner diameter D3 and outer diameter D4 return to their original, resting dimensions. The radial deformation is within the elastic range of the clip 115 so that no significant permanent deformation of the clip 115 occurs during flexation.

The clip 115 can be made from many materials, including metallic and non-metallic. In the one embodiment, the clip 115 is an implant grade titanium (Ti-6A1-4V) per ASTM F-136. In another embodiment, the clip 115 is the same material as the head 220 of the fixation element 105.

The Coupling Element

Again with reference to FIG. 3, the coupling element 110 is configured to receive a fixation element 105 and an elongate rod 120. The coupling element 110 has an internal bore 505 that extends through the coupling element 110 along an axis A and defines entry ports near the bottom and near the top of the coupling element 110. The internal bore 505 has a diameter D5 (best shown in FIG. 7A) at its entry port nearest the bottom of the coupling element 110. Diameter D5 is at least as large as diameter D1, the diameter of the distal end 3050 of the upper region 305 of the head 220. Diameter D5, however, is less than diameter D4, the diameter of the outer surface 420 of the clip 115 in its resting state. As will be discussed in more detail below, diameter D4 decreases upon compression of the clip 115 such that diameter D4 becomes less than diameter D5 of the internal bore 505 allowing the head 220 of the fixation element 105 to be received therethrough.

A pair of laterally-opposed, upwardly extending projections 510 are separated by the bore 505. The projections 510 have internal, threaded surfaces 515. In addition, a pair of u-shaped channels 520 extend through the coupling element 110 for receiving therein a rod 120, which can extend along an axis that is transverse to the axis A of the bore 505.

The upper ends of the projections 510 define an entry port near the top of the coupling element 110 that is sized to receive therein, for example a compression nut 605, as described below. The compression nut 605 can have outer threads 610 that are configured to mate with the inner threads on the opposed inner surfaces 515 of the projections 510 of the coupling element 110. As described below, the entry port is sized and shaped to facilitate an easy entry of a compression nut 605 into or over the projections 510 of the coupling element 110.

A bottom saddle 705 and a top saddle 805 are configured to be positioned within the coupling element 110. The saddles 705, 805 each define a contact surface 715, 815 that has a contour selected to complement a contour of the outer surface of the rod 120. In one embodiment, the contact surfaces 715, 815 have rounded contours that complement the rounded, outer surface of the rod 120. However, the contact surfaces 715, 815 can have any shape or contour that complement the shape and contour of the rod 120. The contact surfaces 715, 815 can also be roughed, serrated, ribbed, or otherwise finished to improve the frictional engagement between the saddles 705, 805 and the rod 120. The rod 120 can also be correspondingly roughed, serrated, ribbed, or otherwise finished to further improve the frictional engagement between saddles 705, 805 and the rod 120.

The complementing shapes and contours between the contact surfaces 715, 815 and rod 120 provide a maximum amount of contact area between the saddles 705, 805 and rod 120. For example, the rod 120 is shown having a rounded or convex outer surface. The contact surfaces 715, 815 of the saddles 705, 805 are correspondingly rounded or concave such that the elongate rod 120 can fit snug between the saddles 705, 805 with the contact surfaces 715, 815 of the saddles 705, 805 providing a wide area of contact with the outer surface of the elongate rod 120. It should be appreciated that the contour and shape of the contact surfaces 715, 815 can be varied to match any contour of the outer surface of the elongate rod 120 or in any manner to maximize the amount of grip between the saddles 705, 805 and the elongate rod 120.

The bottom saddle 705 has an internal bore 710 that axially aligns with the bore 505 in the coupling element 110 when the bottom saddle 705 is placed in the coupling element 110. Furthermore, the bottom saddle 705 has a rounded outer surface that includes a pair of pin cavities 720 positioned, for example, on opposed locations on the bottom saddle 705. Each of the cavities 720 aligns with a corresponding pin aperture 525 that extends through the coupling element 110.

The bottom saddle 705 is secured within the coupling element 110 by positioning the saddle 705 between the projections 510 such that each pin cavity 720 in the bottom saddle 705 aligns with a corresponding pin aperture 525 in the coupling element 110. Pins 905a, 905b are then inserted through each pin aperture 525 such that one end of each pin 905a, 905b pokes into a corresponding pin cavity 720. The pins 905a, 905b provide an interfering engagement with the pin cavities 720 and the pin apertures 525 to thereby secure the bottom saddle 705 in place relative to the coupling element 110.

The diameters of the pins 905a, 905b can be smaller than the diameters of the pin cavities 720 so that there is some play therebetween. Furthermore, the pins 905a, 905b can have lengths that extend only partially into the pin cavities 720 to provide some play therebetween. This permits the bottom saddle 705 to "float" in the coupling element 110 such that the position and the orientation of the bottom saddle 705 can be varied slightly. That is, the bottom saddle 705 can be moved slightly upward or downward and from side to side when mounted in the coupling element 110. The bottom saddle 705 can also rotate slightly when mounted in the coupling element 110. Thus, the bottom saddle 705 can movingly adjust into a secure engagement with the elongate rod 120 when compressed against the elongate rod 120 during assembly, as described below.

Still with reference to FIG. 3, the top saddle 805 can be rotatingly mounted within a compression nut 605 that has outer threads 610 that are configured to mate with the threads on the internal surface 515 of the opposed projections 810 of the coupling element 110. In this regard, the top saddle 805 has an upper projection 510 that rotatingly mates with the compression nut 605 and permits the top saddle 805 to rotate and/or tilt relative to the compression nut 605 when attached thereto. When attached, the top saddle 805 is positioned immediately below the compression nut 605. In another embodiment, the top saddle 805 is fixedly attached to the compression nut 605 such that it does not rotate relative to the compression nut 605. In another embodiment, there is no top saddle and the compression nut 605 directly contacts the stabilizer rod 120.

When the compression nut 605 is attached to the top saddle 805, the compression nut 605 is rotatingly coupled to the coupling element 110 by mating the outer threads 610 of the compression nut 605 with the inner threads 515 of the coupling element 110. The compression nut 605 is repeatedly rotated over a 360 degree rotational angle to lower the compression nut 605 into the coupling element 110. The compression nut 605 is described herein as having outer threads 610 that mate with inner threads 515 on the opposed projections 510. As described below, this advantageously permits a thread configuration that prevents projections 510 from spreading apart from one another as the compression nut 605 is screwed into the coupling element 110. However, it should be appreciated that the compression nut 605 can be modified to have an annular shape with internal threads that mate with corresponding outer threads on the opposed projections 510.

In one embodiment, the various components of the assembly 100 are manufactured of an inert material, such as, for example, stainless steel or titanium.

Relationship Between the Clip, Head and Coupling Element

The configuration of the clip 115 on the head 220 of the fixation element 105 allows for the operator to load the fixation element 105 from the bottom of the coupling element 100. The dimensions of the head 220 without the clip 115 installed in the groove 315 are such that the head 220 can be freely inserted through the entry port of the bore 505 nearest the bottom of the coupling element 110. Although, the head 220 can just as easily slide back out the bottom of the coupling element 110 without the clip 115 positioned in the head 220. Thus, the clip 115 retains the head 220 of the fixation element 105 inside the coupling element 110 and prevents it from backing out the bottom of the coupling element 110. Once the clip 115 is installed in the groove 315 of the head 220, the dimensions of the head 220 are such that the head 220 can no longer be freely inserted through the entry port of the bore 505 near the bottom of the coupling element 110. Loading the fixation element 105 into the coupling element 110 from the bottom involves reduction of the outer diameter of the clip 115 by radial compression, to be discussed in more detail below.

Figure 7A:
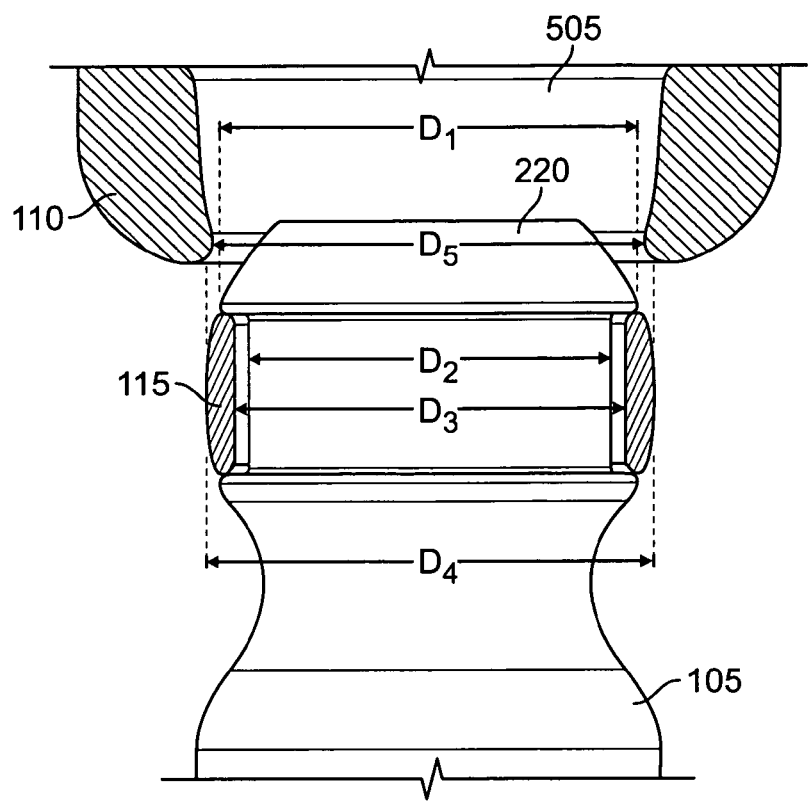
FIGS. 7A and 7B are partially exploded, cross-sectional views of a coupling element and a bone fixation element with clip installed.

FIG. 7A shows the clip 115 in a resting state installed in the groove 315. D1 is the diameter of the distal end 3050 of the upper region 305 of the head 220. In an embodiment, D1 is essentially equal to the diameter of the proximal end 3155 of the lower region 310 of the head 220. D1 constitutes the widest portion of the head 220 of the fixation element 105 when the clip 115 is not installed. D5 is the diameter of the entry port of the internal bore 505 at the bottom of the coupling element 110. D5 is at least as large as D1 allowing for the head of the screw to be freely inserted when the clip 115 is not installed. D2, the diameter of the groove 315, is less than D1.

When installed in the groove 315, the outer surface 420 of the clip 115 completes a generally rounded shape to the head 220 of the fixation element 105. D4 is the outer diameter of the clip 115 when in the resting state. Upon installation of the clip 115 in the groove 315, D4 becomes the widest portion of the head 220. D4 is greater than D1 and also D5. Because D4 is greater than D1 and D5, the head 220 of the fixation element 105 with the clip 115 installed cannot freely pass through the entry port of the internal bore 505 at the bottom of the coupling element 110. Thus, the resting state the head 220 of the fixation element 105 with the clip 115 installed has a diameter that exceeds the diameter of the bore 505.

Figure 7B:
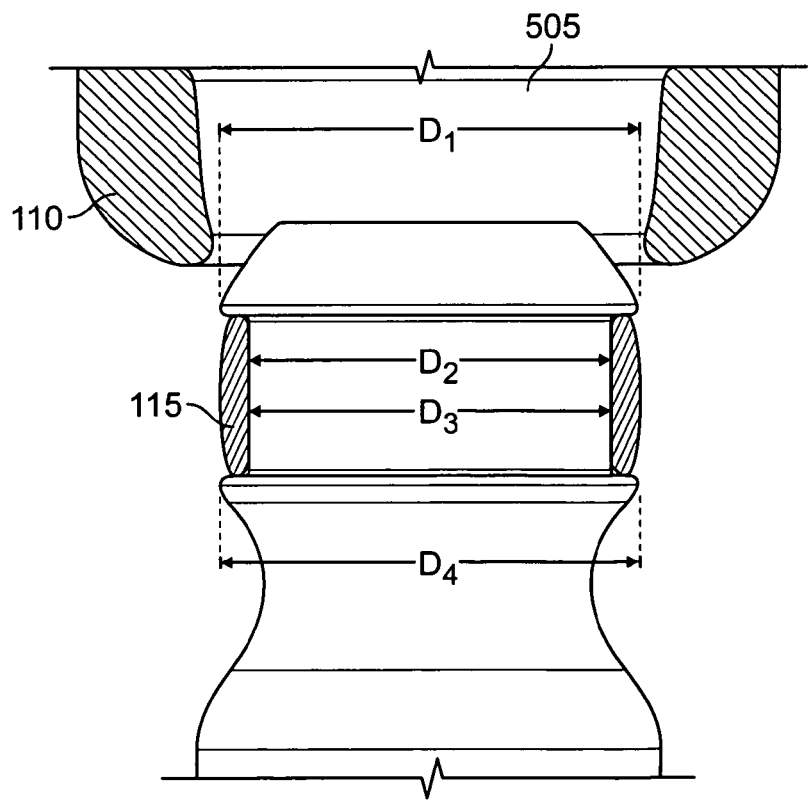

To insert the head 220 through the bore 505 the clip 115 is radially compressed such that D4 becomes less than D5 (see FIG. 7B). As the clip 115 is compressed, the width of the break 405 decreases until the opposing ring surfaces 410, 415 meet and/or the inner surface 425 of the clip 115 abuts the surface of the groove 315. D4 decreases until the head 220 and clip 115 together can be inserted through the entry port at the bottom of the coupling element 110.

Upon insertion of the head 220 of the fixation element 105 into the coupling element 110, the clip 115 expands to its dimensions in the resting state. That is, the clip 115 expands such that diameter D4 is greater than D5 and the head 220 of the fixation element 105 cannot slide back out the entry port of the coupling element 110.

The fixation element 105 rests inside the coupling element 110, the head/clip assembly of which makes contact with a seat 530 near the bottom of the coupling element 110. In one embodiment, the seat 530 is formed of one or more inclined or slanted surfaces. The seat 530 can be formed of an annular surface such that the seat 530 is generally conical or the seat 530 can be formed of three or more flat surfaces, such that the seat is pyramidal. The seat 530 can have any of a variety of shapes adapted to support the head 220 and clip 115 therein. For example, the seat 530 can be spherical, partially-spherical, conical, frustoconical or other shapes. In a preferred embodiment, the seat 530 is conical or at least partially conical.

The seat 530 supports the rounded head/clip assembly of the fixation element 105. The rounded head/clip assembly abuts against the seat 530 near the bottom of the coupling element 110, as shown in the cross-sectional view of FIG. 8. The rounded head/clip assembly contacts the seat 530 along a contact region that can vary in size and shape. The contact region can be in the form of a contact circle for example if the seat 530 is conically shaped. In the instance the seat 530 is conically shaped, the rounded head/clip assembly can be rotated within the seat 530 to move the axis of the shank portion 210 to a desired orientation relative to the coupling element 110 and thereby provide a poly-axial configuration.

Assembly of the Device

The device 100 can be assembled prior to or after driving the fixation element 105 into the bone structure. Similarly, the clip 115 can be assembled in the groove 315 of the fixation element 105 prior to or after driving the fixation element 105 into the bone structure.

In an embodiment, to install the clip 115 into the groove 315, the clip 115 can be inserted over the top of the head 220 of the fixation element 105, for example, when the fixation element 105 is already driven into the bone. Because the inner diameter D3 of the clip 115 is less than the diameter D1 of the upper region 305 of the head 220, the clip expands radially in order to pass over the upper region 305 of the head 220. Once the clip 115 surpasses the upper region 305 of the head 220, the clip slides past the upper lip 320 into the groove 315. The groove has a diameter D2 that is less than the inner diameter D3 of the clip 115. Thus, the clip 115 elastically springs in place such that is returns to its original shape inside the groove 315 between lips 320, 325.

In another embodiment, the clip 115 is installed such that the tip 230 of the fixation element 105 is inserted through the opening 430 in the clip 115, similar to a washer and screw assembly. Because the inner diameter D3 of the clip 115 is greater than the diameter of the shank 210, the clip 115 is easily moved along the length of the fixation element 105. The clip 115 is passed along the shank 210 of the fixation element 105 until it reaches the lower region 310 of the head 220. Because the inner diameter D3 of the clip 115 is less than the diameter of the lower region 310, the clip radially expands in order to pass over the lower region 310 of the head 220. The radial expansion is allowed due, in part, to the break 405 in the clip 115. Once the clip 115 surpasses the lower portion 310 of the head 220, the clip 115 slides past the lower lip 325 into the groove 315. The groove has a diameter D2 that is less than the inner diameter D3 of the clip 115. Thus, the clip 115 elastically springs in place such that it returns to it original shape and is retained inside the groove 315 between lips 320, 325.

Further, the clip 115 can be radially expanded such that the ends 410, 415 of the clip 115 spread apart and allow for the clip 115 to be installed directly into the groove 315 of the head 220 instead of past lips 320 or 325. The ends 410, 415 spread apart such that the width of the break 405 expands and approaches the diameter D2 of the groove 315. The clip 115 is then pushed into the groove 315 between lips 320, 325 and returns to its original shape. A portion of the edge of the clip 115 remains inside the groove 315 and overlaps with lips 320, 325.

To insert the head 220 of the fixation element 105 with the clip 115 installed, through the entry port near the bottom of the coupling element 110, the clip 115 is compressed until D4 is less than D5. The clip 115 can be compressed, for example, with a tool such as a pliers-like tool that radially compresses the clip 115.

In another embodiment, the clip 115 is introduced through the top of the coupling element 110 and the head 220 of the fixation element 105 is introduced through the bottom of the coupling element 110. After the two components (the clip 115 and the fixation element 105) are introduced into the fixation element 105, the clip 115 is coupled to the head 220 while the head is inside the coupling element 110. This is accomplished by expending the clip 115 onto the head 220 of the fixation element 105 until it positions into the groove 315 of the head 220. The clip 15 then collapses into the groove 315. After the assembly, the head 220 of the fixation element 110 is locked in the coupling element 110 such that the head 220 cannot separate from the coupling element 110. In this embodiment, the assembled head/clip does not fit through the bottom opening in the coupling element 110.

As described above, compression of the clip is possible due, in part, to the break 405 in the clip 115; the resting inner diameter D3 of the clip 115 exceeds the diameter D2 of the groove 315; and the flexible nature of the clip 115 material. The clip 115 is compressed until the ends 410, 415 meet and/or D3 approaches D2. Upon insertion of the head 220 into the coupling element 110, the outer diameter D4 of the clip 114 returns to a default diameter that interfaces with the seat to 530 to retain the head 220 within the coupling element 110.

Figure 8:
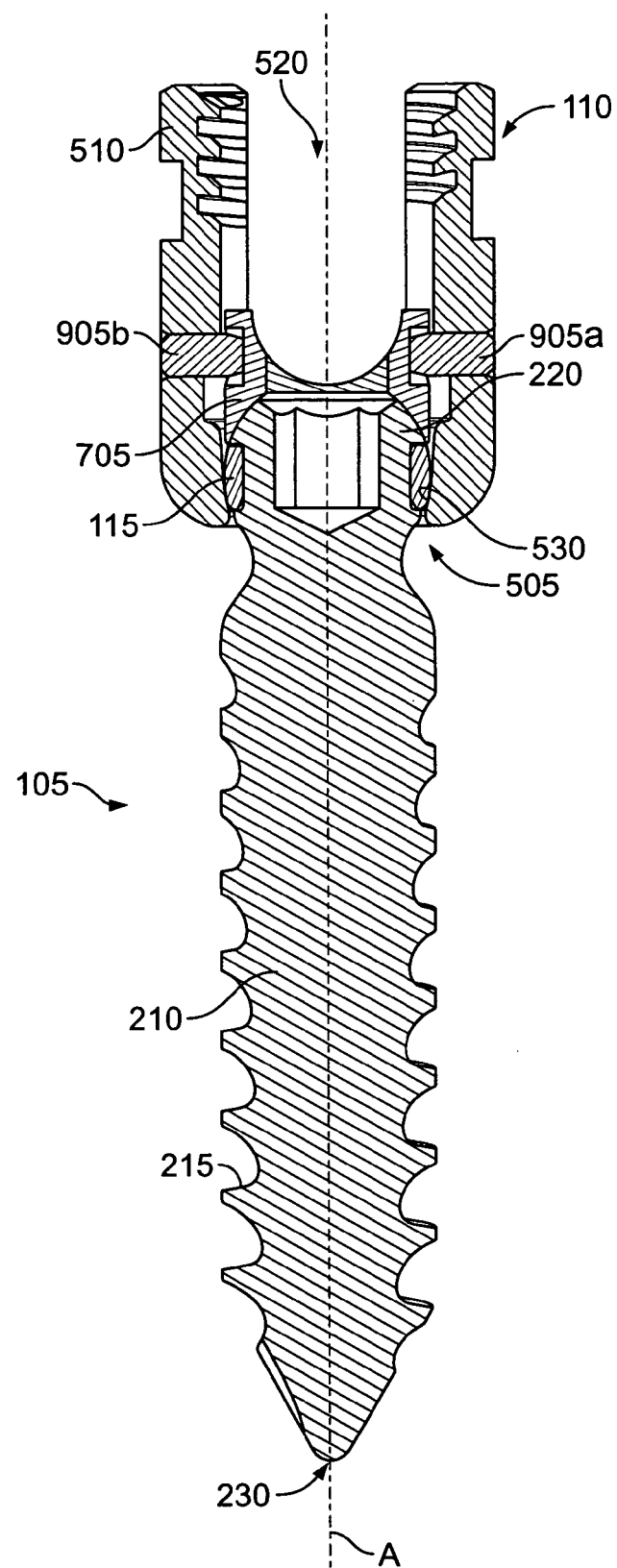
FIG. 8 is a cross-sectional view of a bone fixation assembly.

The rounded head 220 abuts against and sits within a correspondingly-shaped seat 530 in the bottom of the coupling element 110 in a ball/socket manner, as shown in the cross-sectional view of FIG. 8. The seat 530 can have a rounded shape that is configured to provide a secure fit between the head/clip assembly and the coupling element 110. Because the seat 530 is rounded, the head/clip assembly can be rotated within the seat 530 to move the axis of the shank 210 to a desired orientation relative to the coupling element 110 and thereby provide a poly-axial configuration.

With the fixation element 105 positioned in the coupling element 110, the bottom saddle 705 is attached to the coupling element using the pins 905a, 905b, which mate with the pin cavities 720 in the side of the bottom saddle 705. As discussed, there is some play between the pins 905a, 905b and the pin cavities 720, such that the bottom saddle 705 essentially floats and can move somewhat relative to the coupling element 110. That is, the bottom saddle 705 is attached to the coupling element 110 in a manner that permits movement of the bottom saddle 705 relative to the coupling element 110 and/or relative to the elongate rod 120. Thus, the bottom saddle 705 adjusts in position as the compression nut 605 is tightened downward into the coupling element 110, as described below.

The rod 120 is loaded into the coupling element 110 by inserting the rod 120 downwardly between the projections 510 through the unshaped channels 520. As the rod 120 is moved downwardly into the coupling element 110, the outer surface of the rod 120 will eventually abut and sit against the corresponding rounded contact surface 715 of the bottom saddle 705. The compression nut 605 and attached upper saddle 805 are then threaded downward into the coupling element 110 by mating the external threads 610 on the compression nut 605 with the internal threads 515 on the projections 510 of the coupling element 110. The compression nut 605 can be threaded downward until the rod 120 is compressed between the top and bottom saddles 705, 805 with the compression nut 605 providing the compression force.

As mentioned, the coupling element 110 has an entry port for the compression nut 605 that facilitates entry or coupling of the compression nut 605 into the coupling element 110. The entry port is defined by the upper edges of the projections 510. The entry port can have a structure that guides the compression nut 605 into a proper engagement with the coupling element 110. For example, one or more large chamfers can be located on the upper, inner edge of the projections 510 of the coupling element 110 to provide ease of entry for the compression nut 605 into the coupling element 110. The chamfers can be angled with the angle being in the range of thirty degrees to sixty degrees relative to vertical axis A, although the angle can vary. The chamfers can help to guide the compression nut 605 into proper alignment with the coupling element 110 such that the threads 610 on the compression nut 605 properly engage the threads on the opposed projections 510 without any cross-threading.

The compression nut 605 is then threaded downwardly by repeatedly rotating the compression nut 605 about a 360 degree rotation. As the compression nut 605 lowers into the coupling element 110, the rounded contact surface of the top saddle 805 abuts the rod 120 and compresses the rod 120 against the rounded contact surface 715 of the bottom saddle 705. As mentioned the bottom saddle 705 has a floating arrangement with the coupling element 110 and the top saddle 805 is movable and rotatable relative to the compression nut 605. This permits the saddles 705, 805 to gradually reposition themselves into a secure purchase with the rod 120 as the compression nut 605 moves downward. The contact surface of the saddles 705, 805 provide a continuous and maximized area of contact between the saddles 705, 805 and the rod 120 for a secure and tight fit therebetween.

Moreover, the top saddle 805 is shaped so that opposed wings or protrusions 820 are located on opposed sides of the top saddle 805. The opposed protrusions 820 are positioned on either side of the rod 120 so as to automatically guide the saddle 805 into alignment with the rod 120 as the saddle 805 lowers onto the rod 120. Because the top saddle 805 can freely rotate as the compression nut 605 lowers onto the rod 120, the protrusions 820 will abut opposed sides of the rod 120 as the top saddle 805 is lowered into the coupling element 110. The top saddle 805 thus self-aligns into a secure engagement with the rod 120 as the top saddle 805 is lowered onto the rod 120.

In one embodiment, the protrusions 820 of the top saddle 805 are formed by a concave contour of the top saddle contact surface. It should be appreciated that the protrusions 820 need not be formed from curved surfaces, but can also be formed from straight surfaces. Moreover, the protrusions 820 need not be formed from a continuous, elongated surface, but can rather comprise one or more discrete protrusions, such as spikes, that extend downwardly from the top saddle 805.

As the compression nut 605 is threaded downward, the downward force of the compression nut 605 is transferred to the bottom saddle 705 via the top saddle 805 and the rod 120. This causes the bottom saddle 705 to also move downward so as to press downward against the head/clip assembly of the fixation element 105. The head/clip assembly is thereby pressed downward into the seat 530 in a fixed orientation. In this manner, the position of the fixation element 105 relative to the coupling element 110 is fixed. That is, the head/clip assembly of the fixation element 105 is pressed downward into the seat 530 of the coupling element 110 with a force sufficient to lock the position of the head/clip assembly relative to the coupling element 110.

The compression nut 605 can be tightened to provide a sufficient downward force that locks the positions of the saddles 705, 805 relative to the coupling element 110 and the elongate rod 120. The compression nut 605 thereby provides a downward force that locks the relative positions of the elongate rod 120, saddles 705, 805, coupling element 110, and fixation element 105. After this is complete, the upper portion of the opposed projections 510 of the coupling element can be snapped off at a predetermined location along the length of the projections 510.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A spine screw assembly comprising:
   a fastener having an upper end and a lower end, a head at the upper end, and an anchoring element extending between the upper and lower ends, wherein a cylindrical groove is positioned in the head of the fastener;
   an annular clip sized to be positioned in the groove, wherein the annular clip transitions between a first state of increased size and a second state of decreased size, and wherein the annular clip is configured to be slid over the upper end and moved toward the groove when in the first state and to be locked within the groove when unrestrained;
   a coupling element having an upper opening at an upper end and a lower opening at a lower end, the coupling element including a rod receiving channel adapted to receive a stabilizing rod, a bore extending through the lower end of said coupling element for receiving said fastener, and a seat adapted to engage the head when the fastener is positioned in the bore; and
   a compression nut engageable with the coupling element, the compression nut adapted to rotatingly move distally into the coupling element to translate a force to the head of the fastener such that the head is forced against the seat of the coupling element to prevent relative movement between the fastener and the coupling element,
   wherein the head is too large to fit through the lower opening in the coupling element when the annular clip is unrestrained and positioned in the groove and wherein the head and the clip collectively form a spherical shape when the clip is unrestrained and positioned in the groove of the head, wherein the annular clip can be squeezed to a state of further reduced size when the clip is positioned in the groove such that the head and the annular clip can be collectively passed through the lower opening in the coupling element.

2. An assembly as in claim 1, further comprising a rod interposed between the compression nut and the head of the fastener.

3. An assembly as in claim 1, wherein the seat includes a concave surface that supports the head.

4. An assembly as in claim 1, wherein the head is sized to fit through the lower opening in the coupling element only when the annular clip is not positioned in the groove.

5. An assembly as in claim 1, wherein the fastener is a screw.

* * * * *